United States Patent [19]
Ben-Shalom et al.

[11] Patent Number: 6,060,429
[45] Date of Patent: May 9, 2000

[54] COMPOSITION AND METHOD FOR CONTROLLING PLANT DISEASES CAUSED BY FUNGI

[75] Inventors: Noach Ben-Shalom, Tel Aviv; Yigal Elad, Givat Shmuel; Elazar Fallik, Rehovot; Rivka Pinto, Holon, all of Israel

[73] Assignee: State of Israel—Ministry of Agriculture, Israel

[21] Appl. No.: 08/453,651

[22] Filed: May 30, 1995

[30] Foreign Application Priority Data

Jul. 25, 1994 [IL] Israel ......................................... 110446
Apr. 28, 1995 [IL] Israel ......................................... 113548

[51] Int. Cl.$^7$ .................................................. C08B 37/08
[52] U.S. Cl. ......................... 504/116; 504/140; 504/189; 424/93.5; 536/20
[58] Field of Search ........................... 424/93.5; 504/116, 504/189, 140; 536/20

[56] References Cited

U.S. PATENT DOCUMENTS

| | | |
|---|---|---|
| 4,804,750 | 2/1989 | Nishimura et al. |
| 4,970,150 | 11/1990 | Yaku et al. |
| 4,971,956 | 11/1990 | Suzuki et al. |
| 5,068,105 | 11/1991 | Lewis et al. |
| 5,312,908 | 5/1994 | Nakao |
| 5,374,627 | 12/1994 | Ito et al. |

FOREIGN PATENT DOCUMENTS 62-198604  2/1987  Japan .............................. A01N 43/16

OTHER PUBLICATIONS

Gorin, P.A.J., et al., "The chemistry of Polysaccharides of fungi and lichens", The Polysaccharides, vol. 2, Academic Press, 1983, pp. 366–377.

Aldington, S., et al., "Structure–activity relationships of biologically active oligosaccharides", Plant, Cell and Environment, 1991, 14, pp. 625–626.

Hahn, G., et al., "Oligosaccharide elicitors: structures and recognition", Mechanisms of Plant Defense Responses, Kluwer Academic Press, 1993, pp. 99–116.

Fry, S.C. et al., "Oligosaccharides as signals and substrates in the plant cell wall", Plant Physiol, 1993, 103, pp. 1–5.

Hadwiger, L.A., et al., "Chitosan as a component of Pea–*Fusarium solani* interactions", Plant Physiol., 1980, 66, pp. 205–211.

Hirano, S., et al., "Effects of Chitosan, Petric Acid, Lysozyme, and Chitinase on the growth of several Phytopathogens", Agric. Biol. Chem., 53(11), 1989, pp. 3065–3066.

El Ghaouth, A., et al., "Effect of Chitosan on Cucumber plants: suppression of *Pythium aphanidermatum* and induction of defense reactions", The American Phytopathological Society, 83(3), 313–320.

El Ghaouth, A., "Antifungal activity of chitosan on two postharvest pathogens of strawberry fruits", The American Phytopathological Society, 1992, pp. 398–401.

Stossel, P., et al., "Effect of Chitosan, Chitin and some Aminosugars on growth of various soilborne Phytopathogenic fungi", Phytopath. S., 111, 1984, pp. 82–90.

Kendra, D.F., et al., Characterization of the smallest Chitosan Oligomer that is maximally antifungal to *Fusarium solani* and elicits Pisatin formation in *Pisum sativum*, 1984, pp. 276–281.

Allan, C.R., "The fungicidal effect of Chitosan on fungi of varying cell wall composition", Experimental Mycology, 3, 1979, pp. 285–287.

*Primary Examiner*—Leon B. Lankford, Jr.
*Attorney, Agent, or Firm*—Gifford, Krass, Groh, Sprinkle, Anderson & Citkowski, P.C.

[57] ABSTRACT

The invention relates to a method for controlling plant diseases caused by the fungi *Botrytis cinerea* and *Alternaria alternata*, by applying to a growing plant or to fruit or vegetables before or after harvesting, a composition which comprises an effective amount for controlling said fungi of at least one oligosaccharide ingredient, active against *Botrytis cinerea* and *Alternaria alternata*, and selected from oligosaccharides obtainable by hydrolysis of chitin, β-glucan and other similarly active polysaccharides, excluding chitosan, of cell walls of fungi, yeasts, marine plants and exoskeletons of arthropods, The composition also forms part of the invention, as does an analogous method and composition for a method for controlling plant diseases caused by *Botrytis cinerea*, and utilizing at least one oligosaccharide ingredient, active against *Botrytis cinerea* selected from oligosaccharides obtainable by hydrolysis of chitosan, and having a molecular weight within the range of about 500 to about 10,000 daltons, provided that in this instance the composition excludes acetic acid.

3 Claims, 2 Drawing Sheets

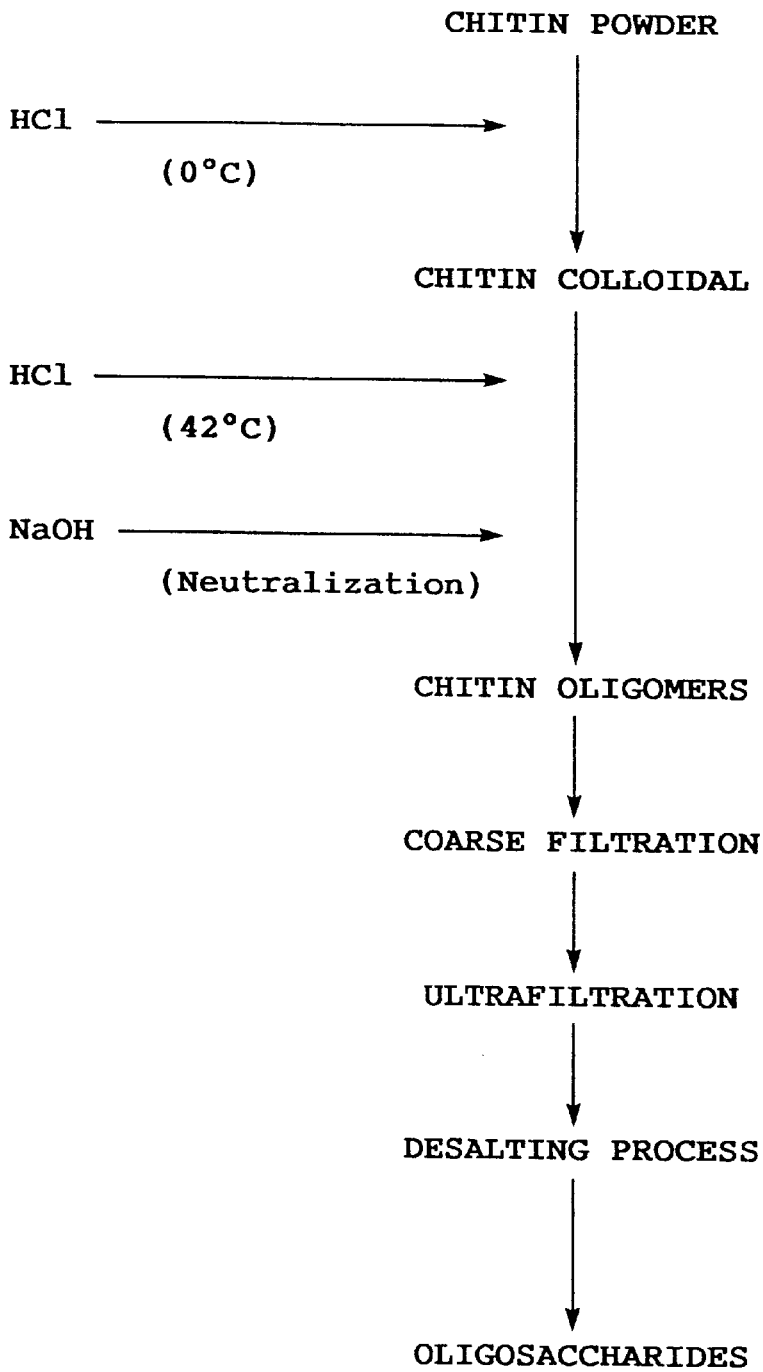
Fig. 1 Flowchart of preparation chitin oligomers.

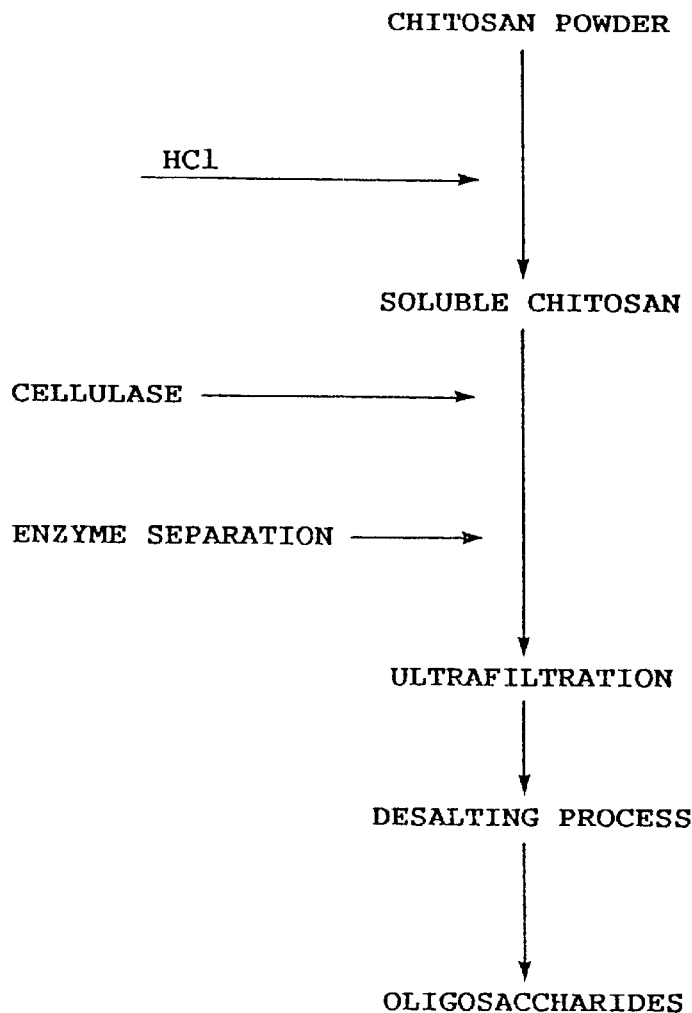
Fig. 2 Flowchart of preparation chitosan oligomers.

COMPOSITION AND METHOD FOR CONTROLLING PLANT DISEASES CAUSED BY FUNGI

FIELD AND BACKGROUND OF THE INVENTION

The present invention relates to a composition and method for controlling plant diseases caused by fungi, in particular *Botrytis cinerea* and *Alternaria alternata,* which utilize substances derived from natural sources.

Gray mold caused by *Botrytis cinerea* and black mold caused by *Alternaria alternata* are serious problems in many crops around the world, both before and after harvesting. These pathogens attack many crops including fruits, vegetables and ornamental plants. Crops are attacked whether grown in the open or under cover. If not adequately controlled, such gray mold and black mold can cause substantial pre-harvest losses, as well as postharvest losses during transport and storage. The pathogens attack all parts of the plants including flowers, fruits, leaves, stems, branches, bulbs or seeds.

The use of chemical fungicides in an attempt to prevent or reduce losses due to such pathogens is fairly widespread, although they give rise to ecological and consumer concerns. Moreover, *B. cinerea* has developed resistance to common fungicides e.g. to dicarboximides and benzimidazoles. In many places, farmers do not have any solution for the problem because of such resistance.

Chitin, which occurs in fungi, yeasts, marine invertebrates and arthropods, may be regarded as cellulose in which the $C^2$—OH groups have been conceptually replaced by acetamido groups. Chitosan is deacetylated chitin. β-glucan is a generally linear polymer composed essentially of β(1-3) D-glucan, but may also be branched and include side-chains of β(1-6) D-glucan. Soluble oligosaccharides are obtained by partial degradation of these polymers. It has moreover been demonstrated that oligosaccharides including those derived from glucan, chitosan and chitin, and which are released from fungal cell walls during plant-fungus interactions are elicitors of plant defense mechanisms (M. G. Hahn et al. in Mechanisms of Plant Defence Responses, B. Fritig and M. Legrand (eds.), Kluwer Academic Publishers (Netherlands), 1993, pages 99–116), while these and other oligosaccharides also have effects on growth and development that are not obviously related to disease resistance (S. C. Fry et al, Plant Physiol 103: 1–5 (1993)). Thus, it is evident that the literature on such oligosaccharides provides only limited information as to whether any particular oligosaccharides will be effective in fighting plant diseases. Further, there is no evidence in the literature that either chemical agents generally, or oligosaccharides in particular, which are effective in controlling certain plant disease will control others; e.g. S. Hirano and N. Nagao in Agric. Biol. Chem. 53, 3065–3066 (1989), reported inter alia that chitosan oligosaccharides inhibit the radial growth in vitro of *Alternaria alternata* (except certain pathotypes) but not *Botrytis cinerea;* and also reported that chitosan (1.0 mg/ml) inhibited the radial growth in vitro of many pathogenic fungi including *Botrytis cinerea* and *Alternaria alternata.*

In vivo, chitosan was shown to inhibit plant disease in low concentrations only in the case of *Fusarium solani* in pea plants in less than 10 μg/ml (L. A. Hadwiger and J. M. Beckman, Plant Physiol. 66, 205–211 (*1980*)), and *Pythium aphanidermatum* in cucumber plants in 100 μg/ml (A. El Ghaouth et al, Phytopathology, 84, 313–320 (1994)). In *Botrytis cinerea* and in *Rizopus stolonifer,* chitosan was shown to inhibit in high concentrations as much as 10 mg/ml (A. El Ghaouth et al, Phytopathology, 82, 398–402 (1992). Allan, C. R., et al., Experimental Mycology 3:285–287 (1979), and Stossel, P., et al., Phytopath. Z., 111:82–90 (1984), both report on antifungal activity of chitin and chitosan, but not of hydrolyzed chitin or chitosan. The mechanism by which chitosan inhibits fungal growth has not been fully elucidated. Kendra, D. F. et al., Experimental Mycology 8: 276–281 (1984), report the results of studies on the anti-*Fusarium solani* activity of chitosan oligomers.

JP 62-198604 describes chitosan hydrolyzates, MW ≦3000, as a control agent for pear black spot due to in particular *Alternaria Alternata* Japanese pear pathotype. Neither this published document nor any other, to the best of the inventors' knowledge, describes chitosan hydrolyzates as a control agent for diseases caused by *Botrytis cinerea.*

U.S. Pat. No. 5,374,627 describes a method for treating plant diseases with a composition including a chitosan hydrolyzate and acetic acid, but does not disclose that such hydrolyzate has any plant disease controlling activity in absence of acetic acid. U.S. Pat. No. 4,970,150 describes and claims an enzymatic method for preparing low molecular weight chitosan oligosaccharides under specific conditions; the product is said to have antibacterial properties, no mention is made of antifungal properties.

SUMMARY OF THE INVENTION

The present invention provides in one aspect a composition for controlling plant diseases caused by fungi selected from *Botrytis cinerea* and *Alternaria alternata,* which comprises an effective amount for controlling said fungi of at least one oligosaccharide ingredient active against *Botrytis cinerea* and *Alternaria alternata,* which oligosaccharide ingredient is selected from oligosaccharides obtainable by hydrolysis of chitin, β-glucan and other polysaccharides (excluding chitosan) of cell walls of fungi, yeasts, marine plants and exoskeletons of arthropods, provided that (a) the composition may comprise additionally at least one carrier, diluent, surface active agent or adjuvant.

The invention moreover provides a method for controlling plant diseases caused by fungi selected from *Botrytis cinerea* and *Alternaria alternata,* wherein there is applied the foregoing composition to a growing plant or to fruit or vegetables before or after harvesting.

In another aspect, the invention provides a composition for controlling plant diseases caused by *Botrytis cinerea,* which comprises an effective amount for controlling said fungus, when applied to a growing plant or to fruit or vegetables before or after harvesting, of at least one oligosaccharide ingredient active against *Botrytis cinerea* which is selected from the group consisting of oligosaccharides obtainable by hydrolysis of chitosan and having a molecular weight within the range of about 500 to about 10,000 daltons, provided that acetic acid is absent from the composition, the composition may comprise additionally at least one carrier, diluent, surface active agent or adjuvant.

The invention moreover provides a method for controlling plant diseases caused by *Botrytis cinerea,* wherein there is applied the foregoing composition to a growing plant or to fruit or vegetables before or after harvesting.

BRIEF DESCRIPTION OF THE DRAWINGS

FIG. 1 is a flowchart relating to the preparation of chitin oligomers which are useful in accordance with an embodiment of the invention.

FIG. 2 is a flowchart relating to the preparation of chitosan oligomers which are useful in accordance with an embodiment of the invention.

DETAILED DESCRIPTION OF THE INVENTION

The oligosaccharides useful in the invention preferably have an average degree of polymerization of 2–50, e.g., 2–24 monomeric units (for example, as determinable by HPLC), and/or a molecular weight (MW) less than about 10,000. In a particular embodiment, the oligosaccharide ingredient comprises oligosaccharides obtainable by (e.g. acid or enzymatic) hydrolysis of chitosan, and have preferably a MW within the range of about 500 to about 10,000 daltons; in the case of enzymatic hydrolysis, the reaction may be quenched by raising the enzymatic hydrolysis reaction mixture to an elevated temperature at which the enzyme is decomposed, or alternatively by passing the enzymatic hydrolysis reaction mixture through a membrane having a 10,000 daltons cut-off. In this connection, it should be noted that oligomers of MW >10,000 are not readily rehydrated after drying, whereas the contrary is true of oligomers of MW <10,000, e.g. of MW in the range about 500 to about 10,000; thus the lower MW range oligomers will be a more useful commercial product. In another embodiment, the oligosaccharide ingredient comprises oligosaccharides obtainable by hydrolysis of chitin and having a MW within the range of about 400 to about 2500 daltons. In yet another embodiment, the oligosaccharide ingredient comprises β-glucan oligomers having a MW within the range of about 200 to about 4300 daltons.

In a particular aspect of the invention, there may be applied additionally at least one microorganism known to control the growth of (or diseases caused by) *Botrytis cinerea* or *Alternaria alternata*, before, simultaneously or after applying the present composition; see, e.g., U.S. Pat. No. 5,266,316 (which relates to use for control of diseases caused by *B. cinerea* and *S. Sclerotiorum*, using *Trichoderma harzianum* I-952 or a derived mutant), the entire contents of which are incorporated by reference herein. The microorganism may be, but need not be, included in the present composition.

Materials and Methods

*Botrytis cinerea* Pers: Fr. was grown on tomato leaf agar at 20° C. Conidia from 10 day old cultures of this pathogen were suspended in water containing 0.01% Tween 80 to give $10^5$–$10^6$ cells/ml.

As exemplary host plants, leaves were collected from 4–7 week old tomato plants, such plants being also used for whole plant experiments. Detached leaves were incubated in 30×45×5 cm plastic trays in a plastic grid that was laid over water-soaked filter paper in order to maintain freshness throughout the course of the experiments. The trays were kept in a transparent polyethylene bag to allow conditions of VPD <1.05 mbar (high RH) and condensation. Pots of whole plants were placed on a water-containing tray and plants were kept under polyethylene bags. Plant materials are kept in an illuminated (1200 lux) walk-in growth chamber at 18° C. for 5–8 days, unless otherwise specified.

Oligosaccharides were applied 24 hours before pathogen inoculation, unless a different spraying sequence is required for localized infection. Detached leaves were inoculated with 30 μl drops containing mixed suspensions of *B. cinerea* and oligosaccharides at 1.2 mg/ml. Up to four treatments (20 drops) were applied to each leaf spaced at least 1 cm apart.

Plant material was inoculated with a conidial suspension of *B. cinerea* containing 0.02M glucose and 0.02M $KH_2PO_4$ to promote infection. The suspension was applied to whole plants by means of an atomizer at a volume of 1.5 ml/plant (ca. 50 μl/leaf), resulting in ca. 50–100 conidia/$cm^2$. Oligosaccharides were applied at 1.2 mg/ml, 24 hours before pathogen inoculation, unless a different spraying sequence is required for localized infection.

Symptoms of the drop-inoculate leaves were evaluated according to a six-score index of intensity of rot underneath the inoculation droplet, where 0=symptomless leaf tissue, 1=1–12% rot, 2=13–25% rot, 3=26–50% rot, 4=51–100% rot underneath the droplet and 5=rot extending about 2 mm around the droplet. Symptoms on whole plants were evaluated according to a severity index of 0–5 where 0=healthy plant and 5=completely destroyed plant (Elad et al., Phytopathol. 84: 1193–1200 (1994) and J. Plant Pathol. 100: 315–336 (1994).

Experiments were arranged in completely randomized or randomized block designs and repeated at least twice. Treatments were replicated 6–12 times in experiments with leaves and whole plants. Data were transformed (Arcsin), analyzed by analysis of variance and tested for significance using Student-Newman-Keul's (SNK) Multiple Range Test.

The invention will now be illustrated by the following examples.

EXAMPLE 1
Production of Chitin Oligomers.

Milled chitin (20 g) from crab shells (Sigma) was stirred with 300 ml of concentrated HCl for 3.0 hr in 0° C., and the suspension of chitin was hydrolyzed by heating the mixture at 42° C. for 1.5 hr. The acidic mixture was neutralized by KOH to pH 4.0, the mixture was centrifuged, the pellet discarded, the supernatant was passed through a membrane having a cut-off of 20,000 M.W., and the effluent was concentrated and then desalted at a membrane with a cut-off of approx. 400–700 MW. For routine working, a mixture of oligomers containing about 1.2% was used, based on acetyl glucoseamine as a standard. The mixture of oligosaccharides was separated on Bio-gel P-4 column, and the different peaks were examined by HPLC; it was found on analysis to contain oligosaccharides with a degree of polymerization of from 2 to 12, i.e. of MW range from about 400 to about 2500 daltons. The production of chitin oligomers is depicted schematically in FIG. 1.

In order to study the optimum conditions for the hydrolysis of chitin to oligosaccharides, the polymer was subjected to different various temperatures and times. As the temperature and time increased, the yield of the oligomers increased, but as shown by HPLC analysis, the average degree of polymerization (DP) in the oligosaccharides has decreased (Table 1).

TABLE 1

Hydrolysis of chitin to oligomers by HCl.

| Temp. | Time | hydrolysis yield (%) | average DP |
|---|---|---|---|
| 42° C. | 2.0 hrs | 9.8 | 4.5 |
| 42° C. | 1.5 hrs | 6.1 | 7.5 |
| 42° C. | 1.0 hrs | 4.2 | 11.3 |
| 32° C. | 2.0 hrs | 2.0 | 11.0 |

EXAMPLE 2
Effect on Radial Growth of *Botrytis cinerea* by Chitin Oligomers.

Control of the growth of *Botrytis cinerea* by oligosaccharides from chitin was studied on dishes supplemented with PDA. A mixture of oligomers with a degree of polymerization in the range of from 2 to 12 was mixed with the agar and the radial growth was checked daily for 3 days compared with the standard. About 45% control of the Botrytis growth was obtained with 6.0 mg/ml oligomers and 31% with 1.2 mg/ml.

TABLE 2

Effect on radial growth of *Botrytis cinerea* by chitin oligomers, in potato dextrose agar.

| Conc. chitin oligomers (mg/ml) | Control of radial growth* (%) |
|---|---|
| 6.0 | 45.2 |
| 1.2 | 31.1 |

*measurement of radial growth performed in three replicates, 3 days after PDA plates were inoculated with *B. cinerea*.

EXAMPLE 3A
Control by Chitin Oligomers of Disease Caused by *Botrytis cinerea* on the Leaves of Tomato Plants.

In order to study the control by chitin oligomers (DP 2–12) of disease caused by *B. cinerea* on the leaves of tomato plants the plants were sprayed with 1.2 mg/ml of the oligomers and 24 hr later were inoculated with the spores ($10^5$) of *B. cinerea*. The severity of the gray mold rot was examined after 5,9 and 14 days. After 5 days the severity of the disease decreased by more than 50% and after 14 days by 22.5% (Table 3).

TABLE 3A

Severity of gray mold disease caused by *Botrytis cinerea* on tomato leaves, treated by chitin oligomers.

| | Disease severity* | | |
|---|---|---|---|
| Treatment | 5 days | 9 days | 14 days |
| Control | 1.13 | 2.46 | 4.15 |
| Oligomers | 0.55 | 2.15 | 3.22 |

*the figures refer to a scale between 0 = no disease and 5 = complete deterioration caused by *Botrytis cinerea*.

EXAMPLE 3B
Control by Chitin Oligomers of Disease Caused by *Botrytis cinerea* on the Detaches Leaves of Tomato Plants.

In order to study the control by chitin oligomers (DP 2–12) of disease caused by *B. cinerea* on the detached leaves of tomato plants the leaves were incubated with 30 μl drops containing 1.2 mg/ml of the oligomers and 24 hr later were inoculated with the spores ($10^5$) of *B. cinerea*. The severity of the gray mold disease was examined after 2, 3 and 4 days. After 2 days the severity of the disease decreased by about 20%, after 3 days by 27% and after 4 days (while the severity of the disease in the control reached a maximum) by 34% (Table 3B).

TABLE 3B

Severity of gray mold disease caused by *Botrytis cinerea* on detached tomato leaves, treated by chitin oligomers.

| | Disease severity* | | |
|---|---|---|---|
| Treatment | 2 days | 3 days | 4 days |
| Control | 2.9 | 4.1 | 5.0 |
| Oligomers | 2.3 | 3.0 | 3.2 |

*the figures refer to a scale between 0 = no disease and 5 = complete deterioration caused by *Botrytis cinerea*.

EXAMPLE 4
Control by Chitin Oligomers of Disease Caused by *Botrytis cinerea* on the Leaves of Bean Plants.

So as to study control by the chitin oligomers (DP 2–12) of disease caused by *Botrytis cinerea* on the leaves of bean plants, the plants were sprayed with 0.6 mg/ml of the oligomers and 24 hr later were inoculated with the spores ($10^5$) of *B. cinerea*. the severity of the gray mold disease was examined after 5, and 9 days. After 5 days the severity of the disease in the bean plants decreased by more than 50% and after 9 days by 22.5% (Table 4).

TABLE 4

Severity of gray mold disease caused by *Botrytis cinerea* on bean leaves, treated by chitin oligomers.

| | Disease Severity* | |
|---|---|---|
| Treatment | 5 days | 9 days |
| Control | 1.13 | 3.12 |
| Oligomers | 0.55 | 2.23 |

*the figures refer to a scale between 0 = no disease and 5 = complete deterioration caused by *Botrytis cinerea*.

EXAMPLE 5
Control by Chitin Oligomers of Disease Caused by *Botrytis cinerea* on the Leaves of Cucumber Plants.

Cucumber plants grown for 6 months in a polyethylene-covered greenhouse were treated with a solution (0.1% w/v) of chitin oligomers (2–12) in an amount of 2 liters per 10 plants and a distribution of 1000 g/ha. Sprays were administered at two dates at the end of the winter growth season (11.3.94 and 18.3.94) and assessment of the disease was carried out on 24.3.94. The base infection rate, before application was 27–30 infection sites per 10 plants. Disease rate on fruits and stems in the comparative untreated plots reached a high rate on the assessment day (Table 5). It was not decreased by iprodione but was significantly reduced by the solution of chitin oligomers.

TABLE 5

Incidence of gray mold on fruits and stems of cucumber plants grown in a commercial greenhouse.

| Treatment | Rate (g/ha) | Fruit infection[1] | Stem infections[1] |
|---|---|---|---|
| Untreated control | — | 60.5 | 36.1 |
| Iprodione[2] | 500 | 65.5 | 45.0 |
| Chitin oligomers | 1000 | 46.7 | 25.6 |

[1]rate of infection per 10 plants 6 days after second treatment.
[2]Iprodione (50 WP Rovral, Rhone Poulenc, France) was sprayed at the recommended dose. Resistance in the population of the pathogen occurred in the greenhouse.

EXAMPLE 6
Control by Combination of Chitin Oligomers with *Trichoderma harzianum* of Disease Caused by *Botrytis cinerea* on Tomato Plant Leaves.

The combined effect of chitin oligomers (DP 2–12) with *Trichoderma harzianum* T-39 (I-952) on tomato leaves was examined. The leaves were sprayed with 2.4 mg/ml of chitin oligomers and $10^6$/ml of the Trichoderma spores. One day later the levels were inoculated with the spores ($10^5$/ml) of *Botrytis cinerea*. The combination of chitin oligomers together with the *T. harzianum* gave much better results as compared with each component separately (Table 6).

TABLE 6

Control of gray mold on tomato leaves using chitin oligomers and/or Trichoderma harzianum T-39 (I-952).

| Treatment | Disease Severity* |
|---|---|
| Control | 2.87 |
| Chitin oligomers (CO) | 2.48 |
| T. harzianum (TH) | 2.58 |
| CO + TH | 1.00 |

*the figures refer to a scale between 0 = no disease and 5 = complete deterioration caused by Botrytis cinerea.

EXAMPLE 7A

Control by Chitin Oligomers of Disease Caused by Botrytis cinerea in Stored Red Tomatoes.

A mixture 0.1% (w/v) of chitin oligomers (DP 2–12; 50 μl) was injected into red tomatoes (variety 144), 2 mm under the skin. Sterile water was injected into the control with a suspension of spores ($10^5$/ml) of Botrytis cinerea which was injected into the fruits, at 0 hours and after 48 hours, in a volume of 30 μl. Later, the fruits were stored at 20° C. and the appearance of the rot was followed during 10 days. Chitin oligomers decreased the quantity of rotted tomato fruits by 50% (Table 7A).

TABLE 7A

Controlling growth of disease caused by Botrytis cinerea by chitin oligomers during storage of red tomatoes.

| Treatment | Time of injecting spores (hours) | Rotted fruits (%) after 10 days |
|---|---|---|
| Control | 0 | 100 |
| " | 48 | 75 |
| Oligomers | 0 | 50 |
| " | 48 | 37 |

EXAMPLE 7B

Control by Chitin Oligomers of Disease Caused by Alternaria alternata in Stored Red Tomatoes.

A mixture 0.12% (w/v) of chitin oligomers (DP 2–12; 50 μl) was injected into red tomatoes (variety 144), 2 mm under the skin. Sterile water was injected into the control fruits. After one day, a suspension of spores ($10^5$/ml) of Alternaria alternata was injected into the fruits in a volume of 30 μl. Later, the fruits were stored at 20° C. and the appearance of the rot was followed during 18 days. After this period of time, 35% of the control fruits were rotted, but 0% of the treated fruits (Table 7B). Thus, chitin oligomers decreased significantly the quantity of tomato fruits rotted by Alternaria alternata.

TABLE 7B

Controlling growth of disease caused by Alternaria alternata by chitin oligomers during storage of red tomatoes.

| Treatment | Time of injecting spores (hours) | Rotted fruits (%) after 18 days |
|---|---|---|
| Control | 24 | 35 |
| Oligomers | 24 | 0 |

EXAMPLE 8

Preparation of Chitosan Oligomers, and Control Therewith of Disease Caused by Botrytis cinerea on the Leaves of Tomato Plants.

Chitosan (9 g), MW=400,000 (Sigma), was suspended in 100 ml water, 100 ml of 0.5N HCl was added to solubilize the chitosan, the pH was adjusted to 5.0 by titration with 0.5N NaOH, the chitosan was diluted to 3%, 0.5% cellulase (Celluclast, Novo) having ≦4 units avicelase activity (per g chitosan) was added, the mixture heated at 50° C. for 6 hours, and the enzymatic reaction was quenched either by heating to 85° C. for 10 minutes, or by passing through a 10,000 daltons cut-off membrane* which removes cellulase and oligomers of MW ≧10,000. After centrifugation, the centrifugate was subjected firstly to membrane* (if not used before) and then to a desalting membrane (cut-off=500 daltons); thus, the product had a MW within the range of about 500 to about 10,000 daltons. Alternatively, chitosan was hydrolyzed using 6N HCl at 100° for 10 hours, with similar subsequent processing. The preparation of chitosan oligomers is depicted schematically in FIG. 2.

Tomato plants were sprayed with 25 μg of the oligomers and 24 hr later were inoculated with spores ($10^5$) of Botrytis cinerea. The severity of the gray mold disease was examined after 6 days. The results showed that the severity of the disease in the tomato plants decreased significantly by use of 25 μg of chitosan oligomers, as shown in Table 8.

TABLE 8

Severity of gray mold disease caused by Botrytis cinerea on tomato leaves, treated by chitosan oligomers.

| | Disease Severity* | |
|---|---|---|
| preparative method: | cellulase | HCl |
| Control | 3.3 | 3.8 |
| Oligomers | 1.7 | 2.1 |

*the figures refer to a scale between 0 = no disease and 5 = complete deterioration caused by Botrytis cinerea.

EXAMPLE 9

Production of β-glucan Oligomers.

β-Glucan oligomers were prepared from 95% laminarin (Sigma) by controlled hydrolysis with 2N trifluoroacetic acid at 85° C. The average degree of polymerization (DP) was 24 units (average MW about 4300) after 10 minutes, 14 units (average MW about 2500) after 20 minutes and 7 units (average MW about 1250) after 30 minutes. β-Glucan oligomers were also prepared from the partially purified cell wall of baker yeast's (saccharomyces cerevisiae) which was hydrolyzed at 100° C. with 50% formic acid for 2 hr, followed by a second hydrolysis with 80% formic acid at 85° C. for 20 minutes and precipitation with 90% alcohol, resulting in oligomers with average DP of 23 units (average MW about 4100).

EXAMPLE 10

Control of Disease Caused by Botrytis cinerea by β-glucan Oligomers During Storage of Red Tomatoes.

In order to study the control of disease caused by Botrytis cinerea, 40 μl of β-glucan oligomer mixture (1–24 subunits; MW in the range of about 200 to about 4300; prepared as in Example 9) in concentration of 1 mg/ml was injected into red tomatoes (variety 144), 2 mm under the skin. Sterile water was injected into the control tomatoes. Two days later the tomatoes were inoculated with $10^5$ spores which were injected therein in a volume of 30 μl., after which they were stored in 20° C. and the appearance of the rot was followed during 10 days. Using laminarin oligomers, we succeeded in reducing rotting of the tomatoes by 50%. β-Glucan oligomers from baker's yeast in the same concentration succeeded in reducing the quantity of rotted tomatoes by 40% (Table 9).

TABLE 9

Controlling growth of disease caused by *Botrytis cinerea* by glucan oligomers during storage of red tomatoes.

| Treatment | Time (hr) | Rotted fruits (%) |
|---|---|---|
| Control Laminarin oligomers | 24 | 100 |
| DP 7 | 24 | 50 |
| DP 14 | 24 | 50 |
| DP 24 | 24 | 50 |
| Yeast oligomers | 24 | 60 |

EXAMPLE 11

Control of Disease Caused by *Alternaria alternata* by β-glucan Oligomers During Storage of Red Tomatoes.

In order to study the control of disease caused by *Alternaria alternata*, 40 μl of a mixture of β-glucan oligomers (1–24 subunits) in a concentration of 1 mg/ml was injected to red tomatoes (variety 144), 2 mm under the skin. Sterile water was injected into the control tomatoes. Two days later they were inoculated with $10^5$ spores which were injected in a volume of 30 μl. Later, the tomatoes were stored in 20° C. and the appearance of the rot was followed during 10 days. Using the oligomers of laminarin to prevent the rot caused by *Alternaria alternata* (Table 10), it can be seen that oligomers with average DP 7 reduced the rotted fruits by 80%, DP 24 by 40%, as oligomers with average DP 14 didn't reduce at all. Oligomers from baker's yeast reduced the severity of the disease by 40% (Table 10).

TABLE 10

Controlling growth of disease caused by *Alternaria alternata* by β-glucan oligomers during storage of red tomatoes.

| Treatment | Time (hr) | Rotted fruits (%) |
|---|---|---|
| Control Laminarin oligomers | 24 | 100 |
| DP 7 | 24 | 20 |
| DP 14 | 24 | 100 |
| DP 24 | 24 | 60 |
| Yeast oligomers | 24 | 60 |

EXAMPLE 12

Control by Laminarin β-glucan Oligomers of Disease Caused by *Botrytis cinerea* on the Leaves of Bean Plants.

In order to study the control of disease caused by *Botrytis cinerea* by laminarin oligomers with average DP of 7–24 (MW in the range of about 1250 to about 4300; prepared as in Example 9) in the leaves of bean plants, the plants were sprayed with 1.5 mg/ml of the oligomers and 24 hr later were inoculated with the spores ($10^5$). The severity of the gray mold disease was examined after 6 days. The results showed that the severity of the disease in the bean plants decreased by all ranges of the oligomers. The most effective one was the oligomer with average DP of 24 subunits (Table 11).

TABLE 11

Severity of gray mold disease caused by *Botrytis cinerea* on bean leaves, treated by laminarin (β-glucan) oligomers.

| Treatment | Disease Severity* |
|---|---|
| Control Laminarin oligomers | 2.3 |
| DP 7 | 1.6 |
| DP 14 | 2.0 |
| DP 24 | 1.2 |

*the figures have the meaning noted above (c.f. Table 8)

While the present invention has been particularly described with respect to its presently preferred embodiments, it will be appreciated by skilled persons that many modifications and variations may be made. Merely by way of example, the compositions of the invention may contain microorganisms, other than or in addition to the *T. harzianum* exemplified herein. Consequently, it will be evident that the invention is not to be construed as restricted to the particularly described embodiments, rather regard will be had to the concept, spirit and scope of the invention, in view of the present disclosure and the claims which follow.

We claim:

1. Composition for controlling plant diseases caused by fungi selected from the group consisting of *Botrytis cinera* and *Alternaria alternata*, which comprises an effective amount for controlling said fungi, when applied to a growing plant or to fruit or vegetables before or after harvesting, of at least one oligosaccharide ingredient active against *Botrytis cinerea* and *Alternaria alternata*, and having a molecular weight of less than about 10,000, which oligosaccharide ingredient is selected from the group consisting of oligosaccharides obtainable by hydrolysis of chitin, β-glucan and other polysaccharides, excluding chitosan, of cell walls of fungi, yeasts, marine plants and exoskeletons of arthropods, provided that the composition may comprise additionally at least one carrier, diluent, surface active agent or adjuvant.

2. Method according to claim 1, wherein there is applied additionally at least one microorganism known to inhibit the growth of, or control plant diseases caused by, *Botrytis cineria* or *Alternaria alternata*.

3. Method according to claim 2, wherein said microorganism is included in said composition.

* * * * *

UNITED STATES PATENT AND TRADEMARK OFFICE
CERTIFICATE OF CORRECTION

PATENT NO. : 6,060,429
DATED : May 9, 2000
INVENTOR(S) : Noach Ben-Shalom et al.

It is certified that error appears in the above-indentified patent and that said Letters Patent is hereby corrected as shown below:

Column 10, lines 35- 48 - Delete entire paragraph and replace with -- 1. A method for controlling plant diseases caused by fungi selected from the group consisting of *Botrytis cinerea* and *Alternaria alternata*, wherein there is applied to a growing plant or to fruit or vegetables before of after harvesting, a composition which comprises an effective amount for controlling said fungi of at least one oligosaccharide ingredient comprises oligosaccharides obtainable by hydrolysis of chitin and having a molecular weight within the range of about 400 to about 2500 daltons, provided that the composition may comprise additionally at least one carrier, diluent, surface active agent or adjuvant. --

Column 10, line 49 - Before "Method" insert -- The--

Column 10, ine 49 - Replace "Method" with --method--

Column 10, line 49 - Delete "accroding to" and insert --of--

Column 10, line 53 - Replace "Method" with --method--

Column 10, line 53 - Delete "according to" and insert --of--

Signed and Sealed this

Seventeenth Day of April, 2001

*Attest:*

NICHOLAS P. GODICI

*Attesting Officer*     *Acting Director of the United States Patent and Trademark Office*